United States Patent [19]

Mück et al.

[11] 4,323,502

[45] Apr. 6, 1982

[54] PROCESS FOR THE SIMULTANEOUS PREPARATION OF TRIOXAN AND CYCLIC FORMALS

[75] Inventors: Karl-Friedrich Mück; Günter Sextro; Karlheinz Burg, all of Wiesbaden, Fed. Rep. of Germany

[73] Assignee: Hoechst Aktiengesellschaft, Frankfurt am Main, Fed. Rep. of Germany

[21] Appl. No.: 81,933

[22] Filed: Oct. 4, 1979

[30] Foreign Application Priority Data

Oct. 5, 1978 [DE] Fed. Rep. of Germany ....... 2843468

[51] Int. Cl.$^3$ ................... C07D 323/06; C07D 317/10
[52] U.S. Cl. .............................. 260/340; 260/340.9 R
[58] Field of Search .................. 260/340.6, 340.7, 338, 260/340.9 R, 340, 340.9

[56] References Cited

U.S. PATENT DOCUMENTS

| | | | |
|---|---|---|---|
| 2,350,350 | 6/1944 | Gresham | 260/338 |
| 2,595,304 | 5/1952 | Schroeder | 260/340.7 |
| 3,998,848 | 12/1976 | Stapp | 260/340.6 |

FOREIGN PATENT DOCUMENTS

| | | | |
|---|---|---|---|
| 748912 | 9/1970 | Belgium . | |
| 1914209 | 10/1970 | Fed. Rep. of Germany . | |
| 48-26032 | 8/1973 | Japan | 260/340 |
| 1012372 | 12/1965 | United Kingdom . | |

OTHER PUBLICATIONS

Chem. Abstracts 59:13970a.

*Primary Examiner*—Ethel G. Love
*Attorney, Agent, or Firm*—Curtis, Morris & Safford

[57] ABSTRACT

A process for the simultaneous synthesis of trioxan and cyclic formals is provided, which comprises reacting a mixture of concentrated formaldehyde and diol and/or epoxide with acid catalysts at a temperature of from 30° to 150° C.

4 Claims, No Drawings

PROCESS FOR THE SIMULTANEOUS PREPARATION OF TRIOXAN AND CYCLIC FORMALS

It is known to manufacture trioxan by cyclization of formaldehyde in aqueous acid solution at elevated temperature (cf. Walker, Formaldehyde Reinhold Publ., New York, 3rd edition 1964, pages 198/199). The acid catalysts used are, for example, strong mineral acids such as sulfuric acid and phosphoric acid or strong organic acids such as p-toluenesulfonic acid or acid ion exchangers (cf. for example U.S. Pat. No. 2,347,447, German Auslegeschrift No. 1,135,491). The trioxan is usually removed from the reaction solution by distillation. The synthesis vapor contains, in addition to trioxan, formaldehyde and water and by-products formed during the synthesis. In most cases it is rectified, for example in the manner described in British Pat. specification No. 1,012,372, in a column provided with a rectifying and stripping part. The fraction obtained which is rich in trioxan is subsequently worked up by extraction and/or by another known separation process.

It is further known to manufacture cyclic formals from diols and formaldehyde or from formaldehyde-yielding substances in the presence of acid catalysts (cf. Walker, Formaldehyde Reinhold Publ. New York, 3rd edition 1964, pages 265,268). The catalysts used in this method are the above-specified acid substances. To obtain the desired formals with high yields, the corresponding alcohols must be used in at least stoichiometrical amounts or in excess (cf. U.S. Pat. No. 2,566,559 and German Auslegeschrift No. 1,293,143). The formals of low boiling points, thsoe that are volatile in steam or form azeotropes with water, are worked up according to the methods described in U.S. Pat. No. 2,395,265 or German Auslegeschrift No. 1,172,687. The synthesis vapor containing formal, water, formaldehyde and by-products stemming from the synthesis, is rectified, and subsequently the distillate rich in formal is further purified by extraction and distillation.

The above-described processes have the disadvantage that both classes of substance are prepared separately from one another and that the diols required for the obtention of the formals must be used in at least stoichiometrical amounts.

A simultaneous synthesis of trioxan and cyclic formals, for example dioxolan, is of great industrial interest for the manufacture of polyacetals, since these substances are used as comonomers in the manufacture of the latter. It was to be expected that the trioxan synthesis would be disturbed considerably in the case of a simultaneous formal synthesis, since trioxan is a currently used starting substance for the manufacture of formals (cf. German Auslegeschriften Nos. 1,293,143 and 1,279,025).

It has now been found surprisingly that the aforesaid disadvantages no longer occur in a process for the simultaneous synthesis of trioxan and cyclic formals, which comprises reacting a mixture of concentrated formaldehyde solution and of from 1 to 25 weight %, preferably 2 to 15%, referred to formaldehyde, of diol and/or epoxides with acid catalysts at a temperature of from 30° to 150° C., preferably of from 100° to 200° C.

The catalysts used in the process of the invention are the compounds known for this purpose, for example phosphoric acid, p-toluenesulfonic acid or acid ion exchangers, preferably sulfuric acid, in an amount of from 2 to 30 weight %, preferably 2 to 10 weight %, referred to the reaction mixture. The formaldehyde solution has generally a strength of from 30 to 80%, preferably 50 to 70%.

The diols used in accordance with the present invention are 1,2-diols, 1,3-diols and $\alpha,\omega$-diols. Instead of the 1,2-diols the corresponding epoxides or mixtures of both can be used. The diols used are preferably those whose cyclic formals have a boiling point below 150° C. and/or form low-boiling azeotropes with water (<150° C.) or are volatile in steam. Examples thereof are ethylene glycol, ethylene oxide, propylene glycol-1,2, propylene oxide, propylene glycol-1,3, butanediol-1,2, butanediol-1,3, butanediol-1,4 and butene-(3)-diol-1,2. Preference is given to ethylene glycol or ethylene oxide, respectively, to propylene glycol-1,2 and to butanediol-1,4, ethylene glycol and ethylene oxide being the most preferred compounds.

The diols are preferably employed in an amount of from 1 to 25 weight %, preferably 2 to 15 weight %, referred to the formaldehyde used.

The simultaneous manufacture of trioxan and cyclic formals can be carried out discontinuously or continuously, preferably continuously. It consists of feeding a vessel provided with agitator or a thermosiphon reboiler with a mixture of aqueous formaldehyde, diol and acid catalyst and metering subsequently a mixture of formaldehyde and diol corresponding to the removal of the reaction product from the reactor, preferably by distillation. The dwell times of the added mixture in the reactor are generally in the range of from 2 to 240 minutes, preferably 15 to 20 minutes.

The results reached with the process according to the present invention can be considered as being surprising since the yields of cyclic formals amount to about 90% of the theory, without using an excess of diol and since the reaction of formaldehyde yielding trioxan is not influenced by the presence of the diol. For example, the yield of trioxan per passage amounts to 30% of the theory when using 65% formaldehyde and hence it is practically at the same level as when trioxan is prepared separately from formaldehyde of the same concentration. This signifies that the process according to the invention permits a better utilization of the feed formaldehyde and it is hence a more economic way of preparing trioxane and cyclic formaldehydes than the conventional processes. A further advantage of the process of the invention resides in the fact that it uses mixtures of formaldehyde and diols that are far more stable than formaldehyde solutions of the same concentration used separately. Thus the formaldehyde solutions are easier to handle and the formaldehyde concentrations can be higher than those in the known isolated trioxan preparation process. Finally the process according to the invention has the advantage that the comonomers used for the manufacture of polyacetals, which are trioxan and for example dioxolan, can be obtained in the desired weight ratios in one operation and in one receptacle.

The reaction mixture containing trioxan, cyclic formal, water, formaldehyde and by-products of the synthesis such as formic acid, is distilled under normal pressure, under reduced pressure or under increased pressure, preferably under normal pressure. The further workup is carried out in usual manner, for example by rectification analogously to the process of British Patent specification No. 1,012,372. The resulting fraction which is rich in trioxan and formal can be split up by extraction, for example using methylene chloride and be purified by subsequent neutralization and distillation. Further known separation processes can likewise be used, for example those described in Process Economics Program Report 23 (1967), page 181 or in German Offenlegungsschrift 1,570,335.

The following examples illustrate the invention. Percentages are by weight.

EXAMPLES 1 to 7

A continuously operating laboratory apparatus provided with a heated agitator flask and a metering device is set with a mixture consisting of 50% formaldehyde, 40% water and 10% sulfuric acid and the mixture is heated to boil the same. A mixture consisting of formaldehyde and varying quantities of diol, as listed in the following table, is metered in a quantity corresponding to that of the reaction mixture which is distilled from the mixture. The dwell time of the reaction mixture in the reactor is 1 hour, the test duration is 4 hours each time. The yield of trioxan and of formal per passage and the nature of the formal obtained can also been seen from the table.

One comparative test is carried out without using diol, that is to say only 65% formaldehyde is used. In this case the trioxan yield is approximately 30%.

| Example | Feed mixture | Yield of trioxan per passage % | Yield of formal per passage % | Formal |
|---|---|---|---|---|
| 1 | 65% CH$_2$O 1% Ethylene glycol* | 92 | 92 | Dioxolan |
| 2 | 65% CH$_2$O 7% Ethylene glycol* | 30 | 87 | Dioxolan |
| 3 | 65% CH$_2$O 15% Ethylene glycol* | 29 | 96 | Dioxolan |
| 4 | 65% CH$_2$O 25% Ethylene glycol* | 29 | 92 | Dioxolan |
| 5 | 65% CH$_2$O 5% Propanediol-(1,2)* | 30 | 98 | 4-Methyldioxolan |
| 6 | 65% CH$_2$O 10% Propanediol-(1,2)* | 30 | 99 | 4-Methyldioxolan |
| 7 | 65% CH$_2$O 15% Propanediol-(1,2)* | 31 | 84 | 4-Methyldioxolan |
| Comparison | 65% CH$_2$O | 30 | — | — |

*Remainder, referred to 100% = water

What is claimed is:
1. A process for the simultaneous synthesis of trioxan and dioxolan, which comprises reacting a mixture consisting of 50% to 70% concentrated aqueous formaldehyde and of from 1 to 25 weight percent, referred to formaldehyde, of ethylene glycol or ethylene oxide with an acid catalyst, at a temperature of from 30° to 150° C.
2. The process as defined in claim 1, wherein ethylene glycol, is a reactant.
3. The process as defined in claim 1, wherein ethylene oxide is a reactant.
4. The process as defined in claims 2 or 3, which comprises using as catalyst sulfuric acid.

* * * * *